(12) United States Patent
Nesvadba et al.

(10) Patent No.: US 8,134,009 B2
(45) Date of Patent: Mar. 13, 2012

(54) PROCESS FOR THE OXIDATION OF SECONDARY AMINES INTO THE CORRESPONDING NITROXIDES

(75) Inventors: Peter Nesvadba, Marly (CH); Lucienne Bugnon, Pfeffingen (CH); Martin Von Büren, Muttenz (CH)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 12/854,677

(22) Filed: Aug. 11, 2010

(65) Prior Publication Data
US 2010/0305322 A1 Dec. 2, 2010

Related U.S. Application Data

(63) Continuation of application No. 10/549,526, filed as application No. PCT/EP2004/050315 on Mar. 17, 2004, now abandoned.

(30) Foreign Application Priority Data

Mar. 27, 2003 (EP) .................................... 03100790

(51) Int. Cl.
| | | |
|---|---|---|
| C07D 211/00 | (2006.01) | |
| C07D 213/72 | (2006.01) | |
| C07D 401/00 | (2006.01) | |

(52) U.S. Cl. ......................... 546/304; 546/184; 546/207
(58) Field of Classification Search .................. 546/304, 546/184, 207
See application file for complete search history.

(56) References Cited

U.S. PATENT DOCUMENTS

| 3,536,720 | A | 10/1970 | Murayama et al. |
| 6,538,141 | B1 | 3/2003 | Gillet et al. |
| 2004/0002606 | A1 | 1/2004 | Detrembleur et al. |
| 2004/0077873 | A1 | 4/2004 | Guerret et al. |

FOREIGN PATENT DOCUMENTS

| DE | 1 695 749 | 4/1971 |
| JP | 2002534409 A | 10/2002 |
| JP | 2004067680 A | 3/2004 |
| WO | WO-0040550 A1 | 7/2000 |
| WO | 02/48159 | 6/2002 |

OTHER PUBLICATIONS

Hawley G.G., The Condensed Chemical Dictionary, $8^{th}$ ed., 1971, pp. 790, 829.
English language Abstract of JP 2004-067680A, Espacenet website (last visited Aug. 19, 2011).

Primary Examiner — Taylor Victor Oh
(74) Attorney, Agent, or Firm — Drinker Biddle & Reath

(57) ABSTRACT

The invention relates to a process for the preparation of secondary nitroxide radicals from their corresponding secondary amines by oxidation with an organic peracid, comprising the steps a) adding to a reaction vessel a secondary amine, optionally together with an organic solvent and in one batch a base selected from the group consisting of alkali metal, alkaline earth metal or ammonium bicarbonates and alkaline earth metal or ammonium carbonates or mixtures thereof in the form of a solid together with water or as an aqueous slurry; b) dosing a peracid under stirring to the reaction mixture in an amount of 1.0 to 2.5 mol per mol of secondary amine; and c) isolating the organic phase.

17 Claims, No Drawings

PROCESS FOR THE OXIDATION OF SECONDARY AMINES INTO THE CORRESPONDING NITROXIDES

Nitroxides, in particular nitroxides of 2,2,6,6-tetraalkyl piperidine, are a very important class of compounds for various industrial applications. They are, for example, used as inhibitors to prevent premature polymerization of vinyl aromatic monomers during purification and distillation. They are also known as efficient stabilizers for organic materials, such as for thermosetting or thermoplastic polymers. Further applications for nitroxides are oxidation catalysts, polymerization regulators in controlled radical polymerization processes and spin labeling agents.

Numerous methods exists for their preparation. Some are for example described in L. B. Volodarsky, V. A. Reznikov, V. I. Ovcharenko: "Synthetic Chemistry of Stable Nitroxides", CRC Press, Boca Raton, 1994. Oxidation of suitable secondary amines is among the most versatile ones.

Different oxidants can be used. From an industrial point of view, hydrogen peroxide, optionally together with various catalysts, t-butylhydroperoxide or peracids, in particular peracetic acid, are useful oxidants.

Peracids bring about a fast and often quantitative oxidation of the amine. They are particularly suitable for the oxidation of amines, which are difficult or impossible to oxidize with hydrogen peroxide, for example of highly sterically hindered amines.

One important parameter for the successful oxidation with a peracid is the pH of the reaction mixture. Thus, if the pH is too low, the oxidation may become too slow because the amine is exhaustively protonated. On the other side, if the pH is raised too much by the addition of a strong base such as e.g. sodium hydroxide, the peracid may decompose under evolution of $O_2$. This leads to the failure of the oxidation and poses additionally a serious security risk, as the oxygen may form an explosive mixture with possibly present volatile organic compounds.

In WO 00/40550 it is suggested to solve this problem by adding simultaneously together with the peracid to the reaction mixture an aqueous solution of for example an alkali metal carbonate or bicarbonate. Peracid and base are simultaneously added as aqueous solutions to the stirred emulsion of water and amine, which is pre-dissolved in an appropriate organic solvent. The dosing rates of peracid and base are regulated in such a way that the pH is maintained in the range of 4 to 12.

Although this is a feasible method, such mode of operation gives raise to serious drawbacks:
a) The apparatus must be equipped with two dosing units.
b) Measuring of the pH is required. However, a reliable pH-measurement in heterogeneous mixtures is rather difficult, in particular in large scale production,
c) Alkali metal bicarbonates have a rather low solubility in water. As a consequence, large volumes of solutions are required. Therefore, the volume yield is low, which negatively influences the economics of the operation.

These drawbacks make the prior art process less attractive for large-scale industrial oxidation processes.

The instant invention avoids these drawbacks and allows thus a substantially more efficient process, particularly when large-scale production is envisaged.

The invention relates to a process for the preparation of secondary nitroxide radicals from their corresponding secondary amines by oxidation with an organic peracid, comprising the steps
a) adding to a reaction vessel a secondary amine, optionally together with an organic solvent and in one batch a base selected from the group consisting of alkali metal, alkaline earth metal or ammonium bicarbonates and alkaline earth metal or ammonium carbonates or mixtures thereof in the form of a solid together with water or as an aqueous slurry;
b) dosing a peracid under stirring to the reaction mixture in an amount of 1.0 to 2.5 mol per mol of secondary amine; and
c) isolating the organic phase.

Adding a base in one batch according to the invention means, that the total amount is added in one single batch, in contrast to dosing it in small portions.

Preferably the organic solvent used in step a) is immiscible with water.

Examples are aromatic solvents, saturated hydrocarbon solvents or ketones.

The peracid may be any organic peracid, for example performic, peracetic, perpropionic, perbenzoic, m-chloroperbenzoic or trifluoroperacetic acid. Preferred is peracetic acid. The peracid may be used pure or in a suitable solvent. Preferred is the solution of peracetic acid in water or in acetic acid.

Preferably the amount of water added in step a) is sufficient to dissolve the organic acid salt formed in the neutralization reaction between the organic acid and the bicarbonate or carbonate.

The overall oxidation reaction is represented by the following equation:

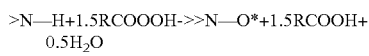
$$>N-H + 1.5 RCOOOH \rightarrow >N-O^* + 1.5 RCOOH + 0.5 H_2O$$

The buffering bases of the present invention are for example bicarbonates of alkali metals and alkaline earth metals (group 1+2 elements) or ammonium bicarbonate or carbonates of alkaline earth metals (group 2 elements) or ammonium carbonate. Mixed salts such as for example dolomite $CaCO_3 \times MgCO_3$ can also be used.

The bicarbonates or carbonates may also be partially replaced by alkaline metal hydroxides or alkaline earth metal hydroxides, for example sodium hydroxide, calcium hydroxide or magnesium hydroxide.

Useful are for example also basic carbonates of alkaline earth metals of a general formula $$nMCO_3 \times mM(OH)_2$$ $n, m$ are integers between 1-10.

The buffering process consists of a partial or complete neutralization of the formed acid RCOOH according for example to:

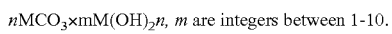
$$nRCOOH + M(HCO_3)_n \rightarrow (RCOO)_nM + nCO_2 + nH_2O$$

when M is an alkali metal cation ($Li^+$, $Na^+$, $K^+$, ...) or $NH_4^+$, then n=1
when M is an alkaline earth metal cation ($Ca^{++}$, $Mg^{++}$, ...), then n=2
Or if an alkaline earth metal carbonate, for example $CaCO_3$, is used:

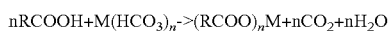
$$2RCOOH + MCO_3 \rightarrow (RCOO)_2M + CO_2 + H_2O$$

The minimal volume of water in the process disclosed in WO 00/40550 for a given amount of bicarbonate is determined by its solubility in water at the given temperature. On the other hand, no or only little water is needed in the process of the present invention. Conveniently, a minimal amount of water may be added in the process of the present invention to ensure the formation of a homogeneous aqueous layer of the neutralized acids. Its amount is for example given by the solubility of the corresponding salts resulting from the organic peracid, for example acetates, if peracetic acid is used.

For example, when sodium bicarbonate ($NaHCO_3$) is used as base, the weight ratio of $NaHCO_3$ to water is typically from 1.5:1 to 0.75:1.

The carbonates of alkaline earth metals, such as for example $CaCO_3$, $MgCO_3$ or Dolomite ($CaCO_3 \times MgCO_3$) have such a low solubility in water that usefully concentrated solutions cannot be prepared. Thus, these carbonates would lead to an extremely low volume yield in the process disclosed in WO 00/40550.

A considerable further advantage of the above mentioned weak bases is that their aqueous slurries do not trigger fast decomposition of the peracid. The difficult measurement of pH in a heterogeneous reaction system is therefore not necessary in the instant process. It is, however, mandatory in the prior art process.

To illustrate this, the solubility data of the technically most important bicarbonates and acetates are presented in Table 1.

TABLE 1

| Solubility | Na$^+$ | K$^+$ | (NH$_4$)$^+$ | Ca$^{2+}$ | Mg$^{2+}$ |
|---|---|---|---|---|---|
| Bicarbonate | 10.3 (25° C.)$^a$ | 36.2 (25° C.)$^a$ | 24.8 (25° C.)$^a$ | — | — |
| Acetate | 50.4 (25° C.)$^a$ | 269 (25° C.)$^a$ | 148 (4° C.)$^a$ | 43.7 (0° C.)$^b$ | 65.6 (25° C.)$^a$ |

$^a$g/100 g Water. (CRC Handbook of Chemistry and Physics, 82 nd Edition)
$^b$g/100 g Solution. (R. K. Freier: "Aqueous Solutions", Walter de Gruyter, Berlin 1976)

Table 2 shows the minimal amount of water, calculated with the data from Table 1, which is needed for the preparation of a solution of 1 mol of bicarbonate to be dosed according to WO 00/40550.

The minimal amount of water needed to completely dissolve the acetate formed during the neutralization of 1 mol acetic acid with 1 mol of bicarbonate or 0.5 mol of carbonate loaded as a solid according to the present invention into the reactor is calculated for comparison. The water formed during the neutralization is not taken into consideration.

TABLE 2

|  | NaHCO$_3$ | KHCO$_3$ | NH$_4$HCO$_3$ | CaCO$_3$ | MgCO$_3$ |
|---|---|---|---|---|---|
| mL of H$_2$O WO 00/40550 | 815.5 (25° C.) | 276.5 (25° C.) | 318.5 (25° C.) | Insoluble | Insoluble |
| mL of H$_2$O Present Invention | 162.7 (25° C.) | 36.5 (25° C.) | 52.0 (4° C.) | 180.9 (0° C.) | 108.5 (25° C.) |

Table 2 clearly shows that the amount of the reactor volume occupied by the unproductive aqueous phase is substantially reduced in the process according to the present invention.

For example the base is sodium or potassium bicarbonate, calcium or magnesium carbonate or dolomite.

Special preference is given to sodium or potassium bicarbonate.

For instance the base is added in an amount of from 0.1 to 1.5 equivalent base per 1 equivalent of all acids present, for example from 0.5 to 1.3.

A suitable reaction temperature is between −20° C. and 80° C., preferably between 0° C. and 40° C.

Conveniently the dosage of the peracid is carried out from 10 minutes to 5 hours.

The total reaction time is for example from 30 minutes to 10 hours. The reaction is carried out, for instance, at atmospheric pressure.

The nitroxide radical formed is for example of formula (I)

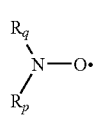

(I)

$R_p$ and $R_q$ are independently tertiary bound $C_4$-$C_{28}$alkyl groups or $C_3$-$C_{17}$ secondary bound alkyl groups which are unsubstituted or substituted by one or more electron withdrawing groups or by phenyl; or $R_p$ and $R_q$ together form a 5, 6 or 7 membered heterocyclic ring which is substituted at least by 4 $C_1$-$C_4$alkyl groups and which may be interrupted by a further nitrogen or oxygen atom.

Consequently the secondary amine precursor is of formula (I')

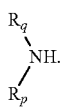

(I')

The amine precursors are mostly items of commerce.

The nitroxyl radicals and their secondary amine precursors are principally known from U.S. Pat. No. 4,581,429 or EP-A-621 878. Particularly useful are the open chain compounds described in WO 98/13392, WO 99/03894 and WO 00/07981, the piperidine derivatives described in WO 99/67298 and GB 2335190 or the heterocyclic compounds described in GB 2342649 and WO 96/24620.

Further suitable nitroxylethers and nitroxyl radicals are described in WO 02/4805 and WO 02/100831

Examples of nitroxyl radicals, which can be prepared by the instant process are given below. For example the nitroxyl radical contains a structural element of formula (X)

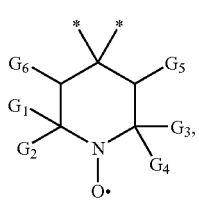

(X)

wherein
$G_1$, $G_2$, $G_3$, $G_4$ are independently $C_1$-$C_8$alkyl or $G_1$ and $G_2$ or $G_3$ and $G_4$, or $G_1$ and $G_2$ and $G_3$ and $G_4$ together form a $C_6$-$C_{12}$cycloalkyl group;
*denotes a valence; and
$G_5$, $G_6$ independently are H or $C_1$-$C_6$alkyl.

Consequently the amine precursor is of formula (X')

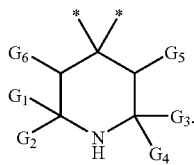
(X')

For instance the nitroxide radical is of formula A', B' or O',

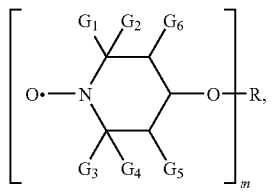
(A')

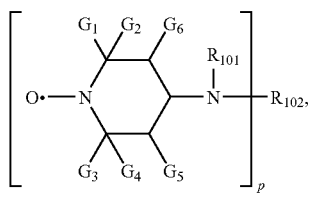
(B')

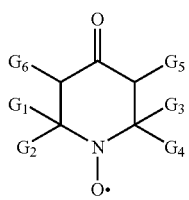
(O')

wherein
m is 1,
R is hydrogen, $C_1$-$C_{18}$alkyl which is uninterrupted or interrupted by one or more oxygen atoms, cyanoethyl, benzoyl, glycidyl, a monovalent radical of an aliphatic carboxylic acid having 2 to 18 carbon atoms, of a cycloaliphatic carboxylic acid having 7 to 15 carbon atoms, or an, -unsaturated carboxylic acid having 3 to 5 carbon atoms or of an aromatic carboxylic acid having 7 to 15 carbon atoms;
p is 1;
$R_{101}$ is $C_1$-$C_{12}$alkyl, $C_5$-$C_7$cycloalkyl, $C_7$-$C_8$aralkyl, $C_2$-$C_{18}$alkanoyl, $C_3$-$C_5$alkenoyl or benzoyl;
$R_{102}$ is $C_1$-$C_{18}$alkyl, $C_5$-$C_7$cycloalkyl, $C_2$-$C_8$alkenyl unsubstituted or substituted by a cyano, carbonyl or carbamide group, or is glycidyl, a group of the formula —$CH_2$CH(OH)—Z or of the formula —CO—Z or —CONH—Z wherein Z is hydrogen, methyl or phenyl;
$G_5$ and $G_6$ are independently hydrogen or $C_1$-$C_4$alkyl, and $G_1$ and $G_3$ are methyl and $G_2$ and $G_4$ are ethyl or propyl or $G_1$ and $G_2$ are methyl and $G_3$ and $G_4$ are ethyl or propyl.

More preferably in formula A', B' and O'
R is hydrogen, $C_1$-$C_{18}$alkyl, cyanoethyl, benzoyl, glycidyl, a monovalent radical of an aliphatic, carboxylic acid;
$R_{101}$ is $C_1$-$C_{12}$alkyl, $C_7$-$C_8$aralkyl, $C_2$-$C_{18}$alkanoyl, $C_3$-$C_5$alkenoyl or benzoyl;
$R_{102}$ is $C_1$-$C_{18}$alkyl, glycidyl, a group of the formula —$CH_2$CH(OH)—Z or of the formula —CO—Z, wherein Z is hydrogen, methyl or phenyl.

The above compounds, their precursors and their preparation are for example described in GB 2335190 and GB 2 361 235. Some are commercially available.

Another group of nitroxyl radicals are those of formula (Ic'), (Id'), (Ie'), (If'), (Ig') or (Ih')

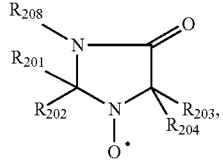
(I'c)

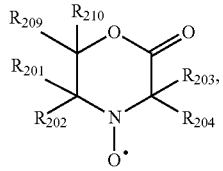
(I'd)

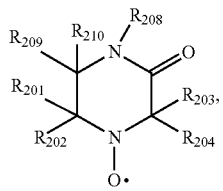
(I'e)

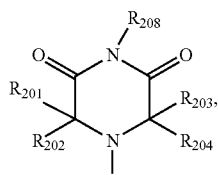
(I'f)

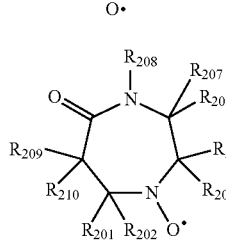
(I'g)

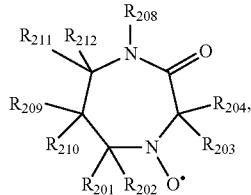
(I'h)

wherein $R_{201}$, $R_{202}$, $R_{203}$ and $R_{204}$ independently of each other are $C_1$-$C_{18}$alkyl, $C_3$-$C_{18}$alkenyl, $C_3$-$C_{18}$alkinyl, $C_1$-$C_{18}$alkyl, $C_3$-$C_{18}$alkenyl, $C_3$-$C_{18}$alkinyl which are substituted by OH, halogen or a group —O—C(O)—$R_{205}$, $C_2$-$C_{18}$alkyl which is interrupted by at least one O atom and/or $NR_{205}$ group, $C_3$-$C_{12}$cycloalkyl or $C_6$-$C_{10}$aryl or $R_{201}$ and $R_{202}$ and/or $R_{203}$ and $R_{204}$ together with the linking carbon atom form a $C_3$-$C_{12}$cycloalkyl radical;
$R_{205}$, $R_{206}$ and $R_{207}$ independently are hydrogen, $C_1$-$C_{18}$alkyl or $C_6$-$C_{10}$aryl;
$R_{208}$ is hydrogen, OH, $C_1$-$C_{18}$alkyl, $C_3$-$C_{18}$alkenyl, $C_3$-$C_{18}$alkinyl, $C_1$-$C_{18}$alkyl, $C_3$-$C_{18}$alkenyl, $C_3$-$C_{18}$alkinyl which are substituted by one or more OH, halogen or a group —O—C(O)—$R_{205}$, $C_2$-$C_{18}$alkyl which is interrupted by at least one O atom and/or $NR_{205}$ group, $C_3$-$C_{12}$cycloalkyl or $C_6$-$C_{10}$aryl, $C_7$-$C_9$-phenylalkyl, $C_5$-$C_{10}$heteroaryl, —O—$C_1$-$C_{18}$alkyl or —COO$C_1$-$C_{18}$alkyl; and $R_{209}$, $R_{210}$, $R_{211}$ and $R_{212}$ are independently hydrogen, phenyl or $C_1$-$C_{18}$alkyl.

More preferably in formula (Ic'), (Id'), (Ie'), (If'), (Ig') and (Ih') at least two of $R_{201}$, $R_{202}$, $R_{203}$ and $R_{204}$ are ethyl, propyl or butyl and the remaining are methyl; or
$R_{201}$ and $R_{202}$ or $R_{203}$ and $R_{204}$ together with the linking carbon atom form a $C_5$-$C_6$cycloalkyl radical and one of the remaining substituents is ethyl, propyl or butyl.

The above compounds, their precursors and their preparation is described in GB 2342649.

Other suitable compounds are the 4-imino piperidine derivatives of formula V

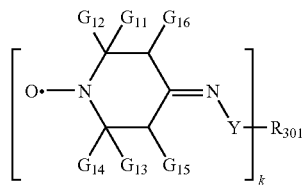

wherein
$G_{11}$, $G_{12}$, $G_{13}$ and $O_{14}$ are independently $C_1$-$C_4$alkyl or $G_{11}$ and $G_{12}$ together and $G_{13}$ and $G_{14}$ together, or $G_{11}$ and $O_{12}$ together or $G_{13}$ and $O_{14}$ together are pentamethylene;
$G_{15}$ and $O_{16}$ are each independently of the other hydrogen or $C_1$-$C_4$alkyl;
k is 1, 2, 3, or 4
Y is O, $NR_{302}$ or when n is 1 and $R_{301}$ represents alkyl or aryl Y is additionally a direct bond;
$R_{302}$ is H, $C_1$-$C_{18}$alkyl or phenyl;
if k is 1
$R_{301}$ is H, straight or branched $C_1$-$C_{18}$alkyl, $C_3$-$C_{18}$alkenyl or $C_3$-$C_{18}$alkinyl, which may be unsubstituted or substituted, by one or more OH, $C_1$-$C_8$alkoxy, carboxy, $C_1$-$C_8$alkoxycarbonyl; $C_5$-$C_{12}$cycloalkyl or $C_5$-$C_{12}$cycloalkenyl;
phenyl, $C_7$-$C_9$phenylalkyl or naphthyl which may be unsubstituted or substituted by one or more $C_1$-$C_8$alkyl, halogen, OH, $C_1$-$C_8$alkoxy, carboxy, $C_1$-$C_8$alkoxycarbonyl;
—C(O)—$C_1$-$C_{36}$alkyl, or an acyl moiety of a, -unsaturated carboxylic acid having 3 to 5 carbon atoms or of an aromatic carboxylic acid having 7 to 15 carbon atoms;
—$SO_3^-Q^+$, —PO($O^-Q^+$)$_2$, —P(O)(O$R_2$)$_2$, —$SO_2$—$R_2$, —CO—NH—$R_2$, —CON$H_2$, COO$R_2$, or Si(Me)$_3$,
wherein $Q^+$ is $H^+$, ammonium or an alkali metal cation;
if k is 2
$R_{301}$ is $C_1$-$C_{18}$alkylene, $C_3$-$C_{18}$alkenylene or $C_3$-$C_{18}$alkinylene, which may be unsubstituted or substituted, by one or more OH, $C_1$-$C_8$alkoxy, carboxy, $C_1$-$C_8$alkoxycarbonyl;
or xylylene; or
$R_{301}$ is a bisacyl radical of an aliphatic dicarboxylic acid having 2 to 36 carbon atoms, or a cycloaliphatic or aromatic dicarboxylic acid having 8-14 carbon atoms;
if k is 3,
$R_{301}$ is a trivalent radical of an aliphatic, cycloaliphatic or aromatic tricarboxylic acid;
and
if k is 4, $R_{301}$ is a tetravalent radical of an aliphatic, cycloaliphatic or aromatic tetracarboxylic acid.

The compounds are described in WO 02/100831.
Preferably $G_{16}$ is hydrogen and $G_{15}$ is hydrogen or $C_1$-$C_4$alkyl, in particular methyl, and
$G_{11}$ and $G_{13}$ are methyl and $G_{12}$ and $G_{14}$ are ethyl or propyl or $G_{11}$ and $G_{12}$ are methyl and $G_{13}$ and $G_{14}$ are ethyl or propyl.

The alkyl radicals in the various substituents may be linear or branched. Examples of alkyl containing 1 to 18 carbon atoms are methyl, ethyl, propyl, isopropyl, butyl, 2-butyl, isobutyl, t-butyl, pentyl, 2-pentyl, hexyl, heptyl, octyl, 2-ethylhexyl, t-octyl, nonyl, decyl, undecyl, dodecyl, tridecyl, tetradecyl, hexadecyl and octadecyl.

Alkenyl with 3 to 18 carbon atoms is a linear or branched radical as for example propenyl, 2-butenyl, 3-butenyl, isobutenyl, n-2,4-pentadienyl, 3-methyl-2-butenyl, n-2-octenyl, n-2-dodecenyl, iso-dodecenyl, oleyl, n-2-octadecenyl oder n-4-octadecenyl.

Preferred is alkenyl with 3 bis 12, particularly preferred with 3 to 6 carbon atoms.

Alkinyl with 3 to 18 is a linear or branched radical as for example propinyl (—$CH_2$—C≡CH), 2-butinyl, 3-butinyl, n-2-octinyl, oder n-2-octadecanyl. Preferred is alkinyl with 3 to 12, particularly preferred with 3 to 6 carbon atoms.

Examples for hydroxy substituted alkyl are hydroxy propyl, hydroxy butyl or hydroxy hexyl.

Examples for halogen substituted alkyl are dichloropropyl, monobromobutyl or trichlorohexyl.

$C_2$-$C_{18}$alkyl interrupted by at least one O atom is for example —$CH_2$—$CH_2$—O—$CH_2$—$CH_3$, —$CH_2$—$CH_2$—O—$CH_3$— or —$CH_2$—$CH_2$—O—$CH_2$—$CH_2$—$CH_2$—O—$CH_2$—$CH_3$—. It is preferably derived from polyethylene glycol. A general description is —(($CH_2$)$_a$—O)$_b$—H/$CH_3$, wherein a is a number from 1 to 6 and b is a number from 2 to 10.

$C_2$-$C_{18}$alkyl interrupted by at least one $NR_5$ group may be generally described as —(($CH_2$)$_a$—$NR_5$)$_b$—H/$CH_3$, wherein a, b and $R_5$ are as defined above.

$C_3$-$C_{12}$cycloalkyl is typically, cyclopropyl, cyclopentyl, methylcyclopentyl, dimethylcyclopentyl, cyclohexyl, methylcyclohexyl or trimethylcyclohexyl.

$C_6$-$C_{10}$ aryl is for example phenyl or naphthyl, but also comprised are $C_1$-$C_4$alkyl substituted phenyl, $C_1$-$C_4$alkoxy substituted phenyl, hydroxy, halogen or nitro substituted phenyl. Examples for alkyl substituted phenyl are ethylbenzene, toluene, xylene and its isomers, mesitylene or isopropylbenzene. Halogen substituted phenyl is for example dichlorobenzene or bromotoluene.

Alkoxy substituents are typically methoxy, ethoxy, propoxy or butoxy and their corresponding isomers.

$C_7$-$C_9$phenylalkyl is benzyl, phenylethyl or phenylpropyl.

$C_5$-$C_{10}$heteroaryl is for example pyrrol, pyrazol, imidazol, 2,4,dimethylpyrrol, 1-methylpyrrol, thiophene, furane, furfural, indol, cumarone, oxazol, thiazol, isoxazol, isothiazol, triazol, pyridine, α-picoline, pyridazine, pyrazine or pyrimidine.

If R is a monovalent radical of a carboxylic acid, it is, for example, an acetyl, propionyl, butyryl, valeroyl, caproyl, stearoyl, lauroyl, acryloyl, methacryloyl, benzoyl, cinnamoyl or β-(3,5-di-tert-butyl-4-hydroxyphenyl)propionyl radical.

$C_1$-$C_{18}$alkanoyl is for example, formyl, propionyl, butyryl, octanoyl, dodecanoyl but preferably acetyl and $C_3$-$C_5$alkenoyl is in particular acryloyl.

Specific examples are:
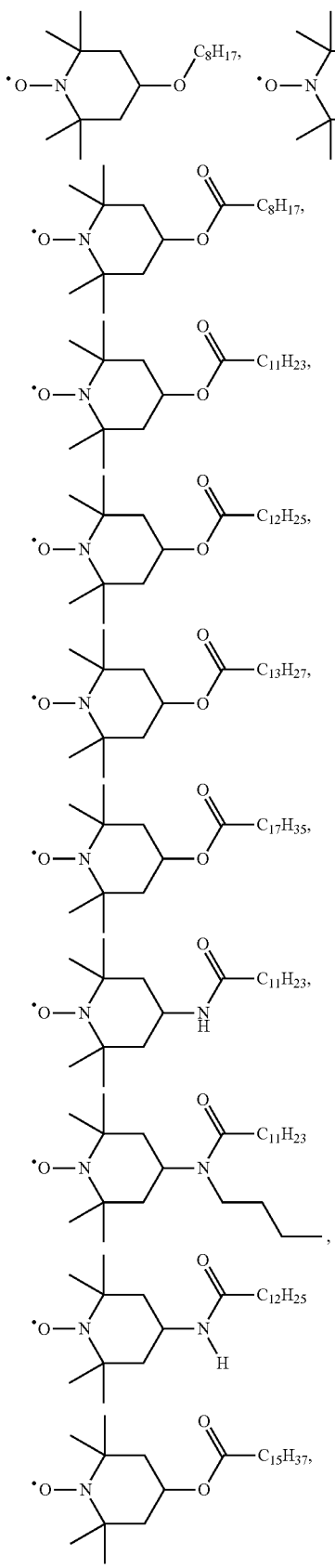
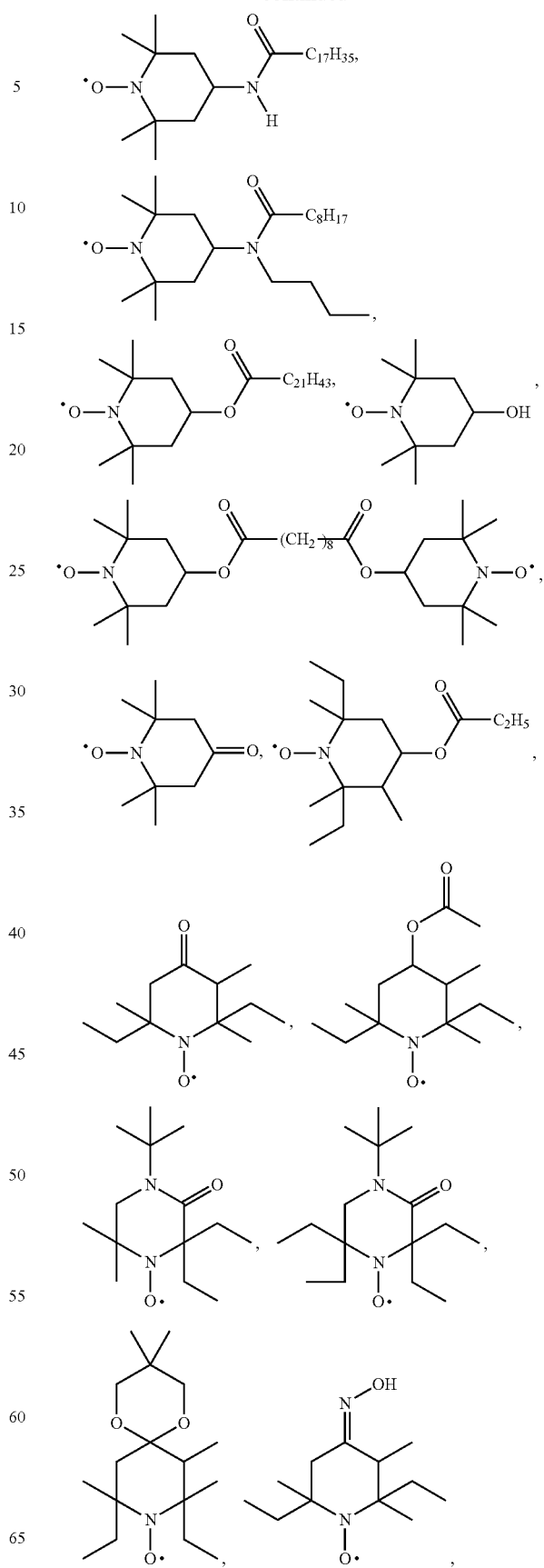

-continued

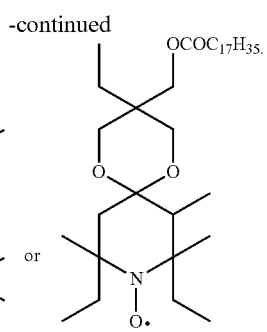

⑦ indicates text missing or illegible when filed

Most preferred are the following compounds:

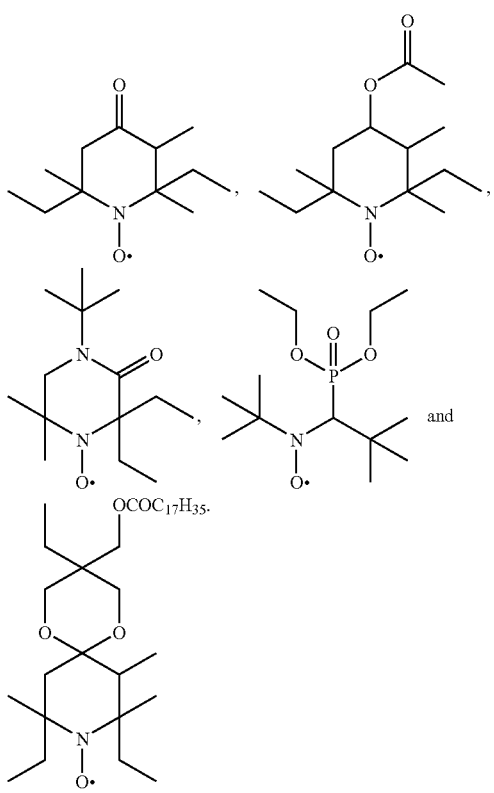

The compounds mentioned above or their amine precursors are partially commercially available or they are prepared by known methods. Higher alkyl substituted piperidines and their preparation are for example described in GB 2 335 190 and in GB 2 361 235.

The following examples illustrate the invention.

EXAMPLE 1

Oxidation of
2,6-Diethyl-2,3,6-trimethyl-piperidine-4-one using
$CH_3COOOH/CaCO_3$ A four neck flask equipped with stirrer, thermometer and dropping funnel is charged with powdered calcium carbonate (20 g, 0.2 mol), water (75 ml), toluene (30 ml) and 2,6-diethyl-2,3,6-trimethyl-piperidine-4-one (19.73 g, 0.1 mol, prepared as described in Ger. Offen. DE 2623422). Peracetic acid (30.4 g, 0.16 mol, 40% solution in acetic acid) is then added dropwise over 50 minutes to the stirred mixture while keeping the temperature between 20-30° C. The mixture is then stirred for additional 150 minutes. The red organic layer is separated, washed with saturated $NaHCO_3$ and water, dried over $MgSO_4$ and evaporated to yield 19.26 g of 2,6-diethyl-2,3,6-trimethyl-piperidin-4-one-N-oxyl as a red liquid. The material is identical with the sample prepared as described in DE 19909767.

EXAMPLE 2

Oxidation of
2,6-Diethyl-2,3,6-trimethyl-piperidine-4-one using
$CH_3COOOH/MgCO_3$ Magnesium carbonate (12.65 g, 0.15 mol) is employed in the same manner as described in example 1, using only 35 ml of water to yield 21.1 g of 2,6-diethyl-2,3,6-trimethyl-piperidine-4-one-N-oxyl as a red liquid. The material is identical with the sample prepared as described in DE 19909767.

EXAMPLE 3

Oxidation of 2,6-Diethyl-2,3,6-trimethyl-piperidine-4-one using $CH_3COOOH/4MgCO_3 \times Mg(OH)_2 \times 5H_2O$ The mixed magnesium carbonate-hydroxide of the formula $4MgCO_3 \times Mg(OH)_2 \times 5H_2O$ (Fluke) (14.56 g, 0.03 mol) is employed in the same way as described in example 2 to yield 20.25 g of 2,6-diethyl-2,3,6-trimethyl-piperidine-4-one-N-oxyl as a red liquid. The material is identical with the authentic sample prepared as described in DE 19909767.

EXAMPLE 4

Oxidation of
2,6-Diethyl-2,3,6-trimethyl-piperidin-4-one using
$CH_3COOOH/NH_4HCO_3$ Ammonium bicarbonate (23.72 g, 0.3 mol) is employed in the same way as described in example 1 using only 20 ml of water to yield 20.52 g of 2,6-diethyl-2,3,6-trimethyl-piperidine-4-one-N-oxyl as a red liquid. The material is identical with the authentic sample prepared as described in DE 19909767.

EXAMPLE 5

Oxidation of
2,6-Diethyl-2,3,6-trimethyl-piperidine-4-one using
$CH_3COOOH/KHCO3$ Potassium bicarbonate (30.03 g, 0.3 mol) is employed in the same way as described in example 1 using only 11 ml of water and 30 ml of ethyl acetate instead of toluene to yield 20.77 g of 2,6-diethyl-2,3,6-trimethyl-piperidine-4-one-N-oxyl as a red liquid. The material is identical with the authentic sample prepared as described in DE 19909767.

EXAMPLE 6

Oxidation of 2,6-Diethyl-2,3,6-trimethyl-piperidine using $CH_3COOOH/NaHCO_3$ A four neck flask equipped with stirrer, thermometer and dropping funnel is charged with sodium bicarbonate (25.20 g, 0.3 mol), water (25 ml), ethylacetate (25 ml) and 2,6-diethyl-2,3,6-trimethyl-piperidine (9.17 g, 0.05 mol, prepared as described in WO 00 46202). Peracetic acid (19.01 g, 0.1 mol, 40% solution in acetic acid) is then added dropwise over 50 minutes to the stirred mixture while keeping the temperature between 20-30° C. The mixture is then stirred for additional 10 hours. The red organic layer is separated, washed with saturated $NaHCO_3$ and water, dried over $Na_2SO_4$ and evaporated to yield 9.63 g of 2,6-diethyl-2,3,6-trimethyl-piperidine-N-oxyl as a red liquid. The material is identical with the authentic sample prepared as described in DE 2621841.

EXAMPLE 7

Oxidation of 2,2,6,6-Tetramethylpiperidin-4-one using $CH_3COOOH/NaHCO_3$

A four neck flask equipped with stirrer, thermometer and dropping funnel is charged with sodium bicarbonate (101.8 g, 1.2 mol), water (100 ml), ethylacetate (100 ml) and 2,2,6,6-tetramethylpiperidin-4-one (31.05 g, 0.2 mol, Aldrich). Peracetic acid (19.01 g, 0. mol, 40% solution in acetic acid) is then added dropwise over 50 minutes to the stirred mixture while keeping the temperature between 20-30° C. The mixture is then stirred for additional 30 minutes. The reaction mass is transferred into a separatory funnel, water (500 ml) is added and the red organic layer is separated. The aqueous layer is extracted with ethyl acetate (2×200 ml). The extracts and the organic layer are combined, dried over $Na_2SO_4$ and evaporated. The oily residue is crystallized from 50 ml hexane to yield 29.6 g of 2,2,6,6-tetramethylpiperidin-4-one-N-oxyl as a red solid. The material is identical with the authentic sample obtained from Aldrich.

EXAMPLE 8

Oxidation of Octadecanoic acid 3,8,10-triethyl-7,8,10-trimethyl-1,5-dioxa-9-aza-spiro-[5.5]undec-3-ylmethyl ester using with $CH_3COOOH/NaHCO_3$ To a stirred solution of 31.35 g (0.1 mol) 3,8,10-triethyl-7,8,10-trimethyl-1,5-dioxa-9-aza-spiro[5.5]undec-3-yl)-methanol (prepared as described in U.S. Pat. No. 4,105,626) in 48 g of toluene were slowly added 30.3 g (0.1 mol) of stearoyl chloride while keeping the temperature between 91-96° C. The mixture after the addition is stirred at room temperature for 12 h. The stirrer is stopped, and the solution of sodium hydroxide (4.2 g, 0.105 mol) in 15 ml water is added at once to the reaction mixture, which is then vigorously stirred for 5 minutes. Then, 25.2 g (0.3 mol) of solid $NaHCO_3$ are added to the reaction mixture. Thereafter, 30.45 g (0.16 mol) of peracetic acid, 40% in acetic acid, are added dropwise within 65 minutes. The inner temperature is kept between 24-33° C. The red emulsion is then stirred at 24° C. for additional 3.5 hours. The red organic layer is transferred into a separatory funnel and is washed twice with 25 ml of deionized water, dried over $MgSO_4$ and evaporated on a rotary evaporator to give 59.35 g (99.7%) of the targeted nitroxide as a red oil.

Elemental analysis: $C_{36}H_{88}NO_5$ (594.95), C: 72.62/72.63% (theory: 72.68%), H: 11.35/11.46% (theory: 11.52%), N: 2.25/2.22% (theory: 2.35%).

What is claimed is:

1. A process for the preparation of secondary nitroxide radicals from their corresponding secondary amines by oxidation with an organic peracid, comprising the steps of:
    a) forming a reaction mixture by adding to a reaction vessel a secondary amine and in one batch either
        an amount of water together with solid $NaHCO_3$, $KHCO_3$, or a mixture thereof; or
        an aqueous slurry of $NaHCO_3$, $KHCO_3$, or a mixture thereof; and
    b) dosing a peracid to the reaction mixture in an amount of 1.0 to 2.5 mol per mol of secondary amine.

2. The process according to claim 1 further comprising adding an organic solvent immiscible with water to the reaction mixture prior to dosing said peracid.

3. The process according to claim 1 wherein the peracid is peracetic acid.

4. The process according to claim 1 wherein the $NaHCO_3$, $KHCO_3$, or mixture thereof is added in an amount of from 0.1 to 1.5 equivalents per 1 equivalent of all acids present.

5. The process according to claim 1 wherein the reaction temperature is between 0° C. and 40° C.

6. The process according to claim 1 wherein dosing the peracid is carried out from 10 minutes to 5 hours.

7. The process according to claim 1 wherein the nitroxide radical is of formula (I)

wherein $R_p$ and $R_q$ are independently tertiary bound $C_4$-$C_{28}$alkyl groups or $C_3$-$C_{17}$ secondary bound alkyl groups which are unsubstituted or by one or more electron withdrawing groups or by phenyl; or $R_p$ and $R_q$ together form a 5, 6 or 7 membered heterocyclic ring which is substituted at least by 4 $C_1$-$C_4$alkyl groups and which may be interrupted by a further nitrogen or oxygen atom.

8. The process according to claim 1 wherein the nitroxide radical is within a structural element of formula (X)

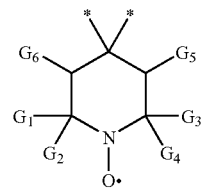

wherein $G_1$, $G_2$, $G_3$, $G_4$ are independently $C_1$-$C_6$alkyl; or $G_1$ and $G_2$ or $G_3$ and $G_4$, or $G_1$ and $G_2$ and $G_3$ and $G_4$ together form a $C_5$-$C_{12}$cycloalkyl group;

*denotes a valence; and $G_5$, $G_6$ independently are H or $C_1$-$C_6$alkyl.

9. A process for the preparation of secondary nitroxide radicals from their corresponding secondary amines by oxidation with an organic peracid, said process comprising the steps of:
   a) forming a reaction mixture by adding to a reaction vessel a secondary amine and in one batch solid $NaHCO_3$, $KHCO_3$, or a mixture thereof; and
   b) dosing a peracid to the reaction mixture in an amount of 1.0 to 2.5 mol per mol of secondary amine;
wherein said forming and said dosing are done in the absence of water.

10. The process according to claim 9 further comprising adding an organic solvent immiscible with water to the reaction mixture prior to dosing said peracid.

11. The process according to claim 9 wherein the peracid is peracetic acid.

12. The process according to claim 9 wherein the $NaHCO_3$, $KHCO_3$, or mixture thereof is added in an amount of from 0.1 to 1.5 equivalents per 1 equivalent of all acids present.

13. The process according to claim 9 wherein the reaction temperature is between 0° C. and 40° C.

14. The process according to claim 9 wherein dosing the peracid is carried out from 10 minutes to 5 hours.

15. The process according to claim 8, wherein the radical is of formula (X):

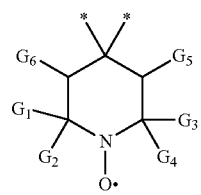

(X)

wherein
$G_1$, $G_2$, $G_3$, $G_4$ are independently $C_1$-$C_6$-alkyl;
*denotes a valence; and
$G_5$, $G_6$ independently are H or $C_1$-$C_6$-alkyl;
from its corresponding secondary amine by oxidation with an organic peracid, comprising the steps
   a) forming a reaction mixture by adding to a reaction vessel a secondary amine, optionally together with an organic solvent and in one batch either an amount of water together with solid $NaHCO_3$, $KHCO_3$, or a mixture thereof or an aqueous slurry of $NaHCO_3$, $KHCO_3$, or a mixture thereof;
   b) dosing a peracid under stirring to the reaction mixture in an amount of 1.0 to 2.5 mol per mol of secondary amine; and
   c) isolating the organic phase.

16. The process according to claim 1, wherein the secondary nitroxide radicals are selected from secondary nitroxide radicals of formula (I):

(I)

wherein
$R_p$ and $R_q$ together form a heterocyclic ring which is substituted at least by four $C_1$-$C_4$-alkyl groups or

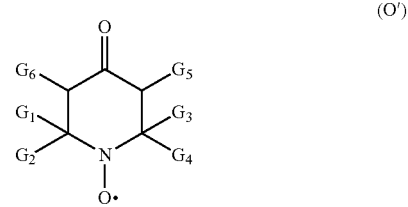

(O')

wherein
$G_5$ and $G_6$ are independently hydrogen or $C_1$-$C_4$-alkyl, and
$G_1$ and $G_3$ are methyl and $G_2$ and $G_4$ are ethyl or propyl or
$G_1$ and $G_2$ are methyl and $G_3$ and $G_4$ are ethyl or propyl, or

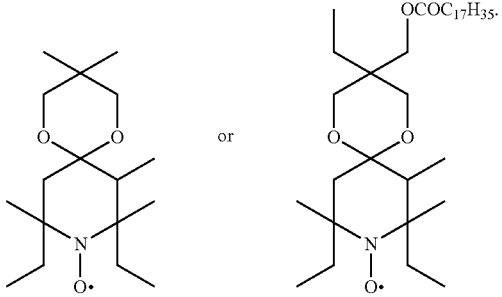

17. A process according to claim 1, wherein the secondary nitroxide radical is chosen from:
   2,6-diethyl-2,3,6-trimethyl-piperidine-4-one;
   2,6-diethyl-2,3,6-trimethyl-piperidine;
   2,2,6,6-tetramethylpiperidin-4-one; and
   octadecanoic acid 3,8,10-triethyl-7,8,10-trimethyl-1,5-dioxa-9-aza-spiro[5.5]undec-3-ylmethyl ester.

* * * * *